United States Patent
Mustufa et al.

(10) Patent No.: US 12,121,309 B2
(45) Date of Patent: Oct. 22, 2024

(54) SYSTEMS AND METHODS FOR NAVIGATING AN ONSCREEN MENU IN A TELEOPERATIONAL MEDICAL SYSTEM

(71) Applicant: INTUITIVE SURGICAL OPERATIONS, INC., Sunnyvale, CA (US)

(72) Inventors: Tabish Mustufa, Sunnyvale, CA (US); Sophia R. Hannaford, Palo Alto, CA (US); Jason S. LaFrenais, San Jose, CA (US); Paul W. Mohr, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 40 days.

(21) Appl. No.: 17/799,766

(22) PCT Filed: Feb. 17, 2021

(86) PCT No.: PCT/US2021/018338
§ 371 (c)(1),
(2) Date: Aug. 15, 2022

(87) PCT Pub. No.: WO2021/167954
PCT Pub. Date: Aug. 26, 2021

(65) Prior Publication Data
US 2023/0073049 A1    Mar. 9, 2023

Related U.S. Application Data

(60) Provisional application No. 62/978,388, filed on Feb. 19, 2020.

(51) Int. Cl.
*A61B 34/00* (2016.01)
*A61B 17/00* (2006.01)
(Continued)

(52) U.S. Cl.
CPC .............. *A61B 34/25* (2016.02); *A61B 34/35* (2016.02); *A61B 34/74* (2016.02); *A61B 90/37* (2016.02);
(Continued)

(58) Field of Classification Search
CPC ......... A61B 34/25; A61B 34/35; A61B 34/74; A61B 90/37; A61B 2017/00199;
(Continued)

(56) References Cited

U.S. PATENT DOCUMENTS 6,742,410 B1 *   6/2004   Eschler ..................... B61L 3/18
                                                     345/157
7,672,692 B2 *   3/2010   Nishino ................ G06F 3/0338
                                                     345/157
(Continued)

FOREIGN PATENT DOCUMENTS

WO    WO-2016077552 A1    5/2016
WO    WO-2018013197 A1    1/2018
(Continued)

OTHER PUBLICATIONS

International Preliminary Report on Patentability for Application No. PCT/US2021/018338, mailed Sep. 1, 2022, 10 pages.
(Continued)

*Primary Examiner* — Andrew T Chiusano
(74) *Attorney, Agent, or Firm* — Haynes & Boone, LLP

(57) ABSTRACT

A system comprises a teleoperational manipulator configured to control operation of a medical instrument in a surgical environment. The system further comprises an operator input system including an input device and a processing unit including one or more processors. The processing unit is configured to display an image of a field of view of the surgical environment and display a menu including a set of directionally arranged menu options. The
(Continued)

processing unit is further configured to transition the input device from a first constraint state for interaction with the medical instrument to a second constraint state for interaction with the menu. In the second constraint state, the input device is constrained to move in one or more directions based on the set of directionally arranged menu options.

20 Claims, 9 Drawing Sheets

(51) Int. Cl.
| | | |
|---|---|---|
| *A61B 34/35* | (2016.01) | |
| *A61B 90/00* | (2016.01) | |
| *G06F 3/01* | (2006.01) | |
| *G06F 3/0346* | (2013.01) | |
| *G06F 3/0354* | (2013.01) | |
| *G06F 3/0362* | (2013.01) | |
| *G06F 3/0482* | (2013.01) | |
| *G06F 3/0487* | (2013.01) | |

(52) U.S. Cl.
CPC ............ *G06F 3/016* (2013.01); *G06F 3/0482* (2013.01); *G06F 3/0487* (2013.01); *A61B 2017/00199* (2013.01); *A61B 2017/00973* (2013.01); *G06F 3/0346* (2013.01); *G06F 3/0354* (2013.01); *G06F 3/0362* (2013.01)

(58) Field of Classification Search
CPC ........... A61B 2017/00973; G06F 3/016; G06F 3/0482; G06F 3/0487; G06F 3/0346; G06F 3/0354; G06F 3/0362
See application file for complete search history.

(56) References Cited

U.S. PATENT DOCUMENTS

| | | | |
|---|---|---|---|
| 11,083,967 B1* | 8/2021 | Summit | A63F 13/285 |
| 2005/0283804 A1* | 12/2005 | Sakata | H04N 21/4332 |
| | | | 725/38 |
| 2014/0316433 A1 | 10/2014 | Navve et al. | |
| 2015/0012010 A1 | 1/2015 | Adler et al. | |
| 2017/0333139 A1* | 11/2017 | Suresh | A61B 34/30 |
| 2019/0231459 A1* | 8/2019 | Mustufa | A61B 90/00 |
| 2020/0222138 A1* | 7/2020 | Diolaiti | A61B 34/37 |

FOREIGN PATENT DOCUMENTS

| | | | | |
|---|---|---|---|---|
| WO | WO-2019010097 A1 | | 1/2019 | |
| WO | WO-2020185218 A1 * | | 9/2020 | A61B 34/20 |

OTHER PUBLICATIONS

International Search Report and Written Opinion for Application No. PCT/US2021/018338, mailed on Jul. 6, 2021, 16 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR NAVIGATING AN ONSCREEN MENU IN A TELEOPERATIONAL MEDICAL SYSTEM

CROSS-REFERENCE TO RELATED APPLICATIONS

This application is the U.S. National Phase of International Application No. PCT/US2021/018338, filed Feb. 17, 2021, which designated the U.S. and claims the benefit of U.S. Provisional Application No. 62/978,388, filed Feb. 19, 2020, entitled "Systems and Methods for Navigating An Onscreen Menu in a Teleoperational Medical System," each of which is hereby incorporated by reference herein in their entirety.

FIELD

The present disclosure is directed to systems and methods for performing a teleoperational medical procedure and more particularly to systems and methods for displaying and navigating a menu using an operator input device.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted. As teleoperational medical systems become more complex, with additional features and interaction modalities, adding additional physical control devices to the operator control station becomes less feasible. To extend the capability of a teleoperational system, graphical menus visible to and accessible by the operator are needed. Accordingly, it would be advantageous to provide improved methods and systems for navigating graphical menus visible and accessible to the operator.

SUMMARY

The embodiments of the invention are best summarized by the claims that follow the description.

Consistent with some embodiments, a system is provided. The system includes a teleoperational manipulator configured to control operation of a medical instrument in a surgical environment. The system further includes an operator input system including an input device. The system further includes a processing unit including one or more processors. The processing unit is configured to display an image of a field of view of the surgical environment. The processing is further configured to display a menu including a set of directionally arranged menu options. The processing unit is further configured to transition the input device from a first constraint state for interaction with the medical instrument to a second constraint state for interaction with the menu. In the second constraint state, the input device is constrained to move in one or more directions based on the set of directionally arranged menu options.

Consistent with other embodiments, a method performed by a processing unit is provided. The method includes displaying an image of a field of view of a surgical environment. The method further includes displaying a menu with the image of the field of view. The menu includes a set of directionally arranged menu options. The method further includes transitioning an input device of an operator input system of a teleoperational assembly from a first constraint state for interaction with a medical instrument of the teleoperational assembly to a second constraint state for interaction with the menu. The method further includes constraining movement of the input device in one or more directions based on the set of directionally arranged menu options when the teleoperational assembly is in the second constraint state.

Other embodiments include corresponding computer systems, apparatus, and computer programs recorded on one or more computer storage devices, each configured to perform the actions of the methods.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

Figure 1A:
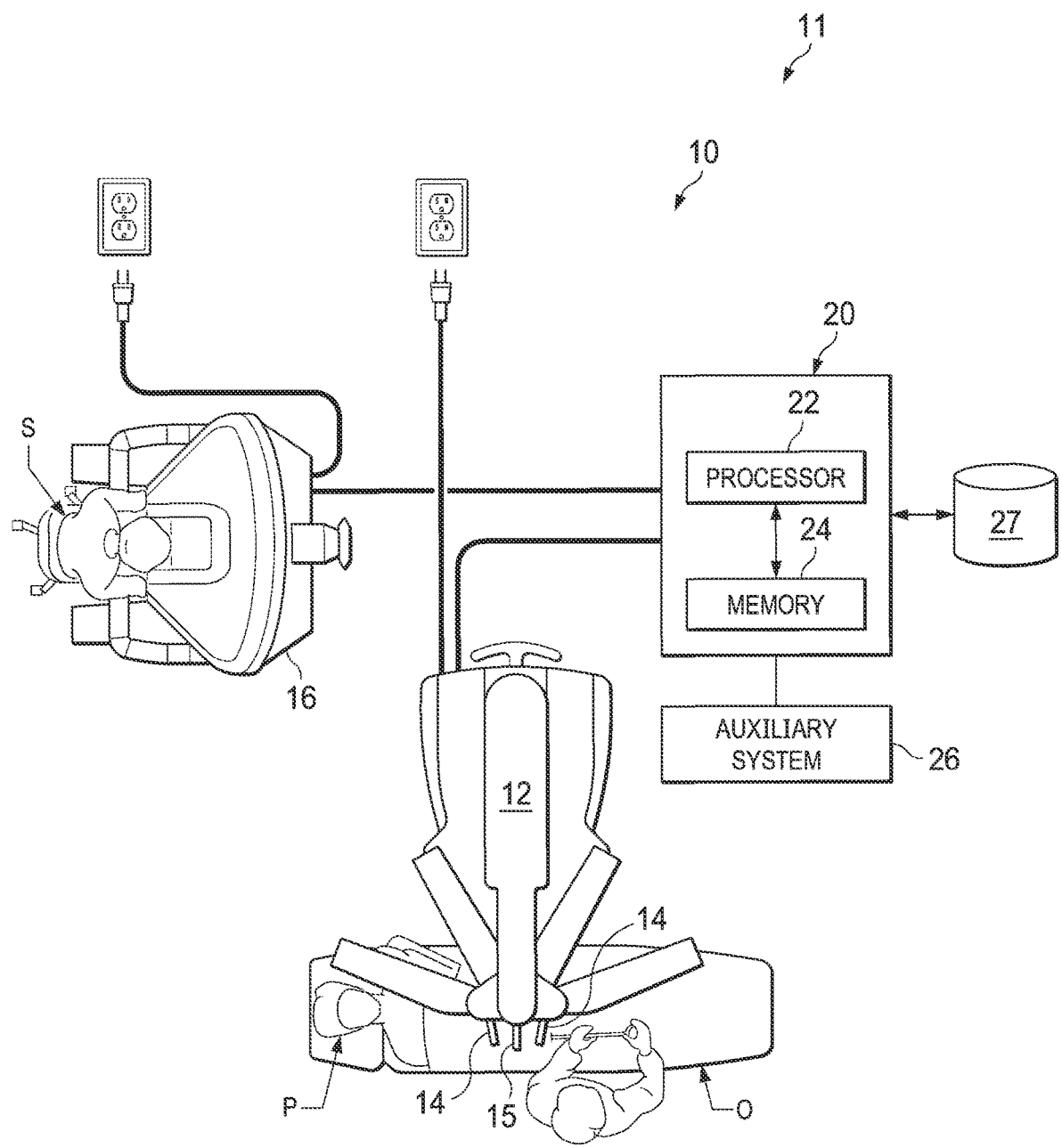
FIG. 1A is a schematic view of a teleoperational medical system according to some embodiments.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following description, specific details describe some embodiments consistent with the present disclosure. Numerous specific details are set forth in order to provide a thorough understanding of the embodiments, it will be apparent to one skilled in the art, however, that some embodiments may be practiced without some or all of these specific details. The specific embodiments disclosed herein are meant to be illustrative but not limiting. One skilled in the art may realize other elements that, although not specifically described, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances well known methods, procedures, components, and circuits have not been described in detail so as not to unnecessarily obscure aspects of the embodiments.

Figure 1B:
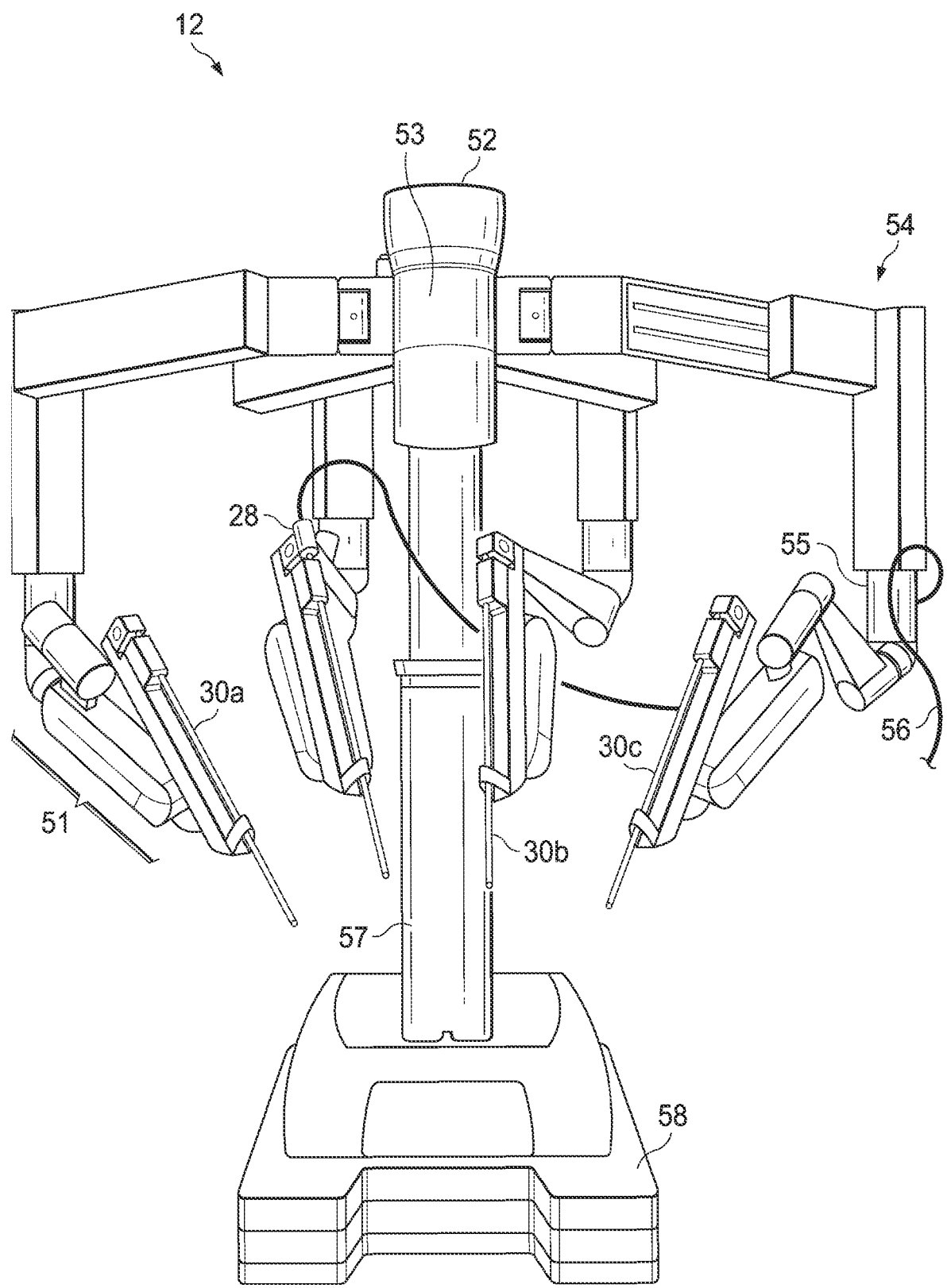
FIG. 1B is a perspective view of a teleoperational assembly according to some embodiments.
Figure 1C:
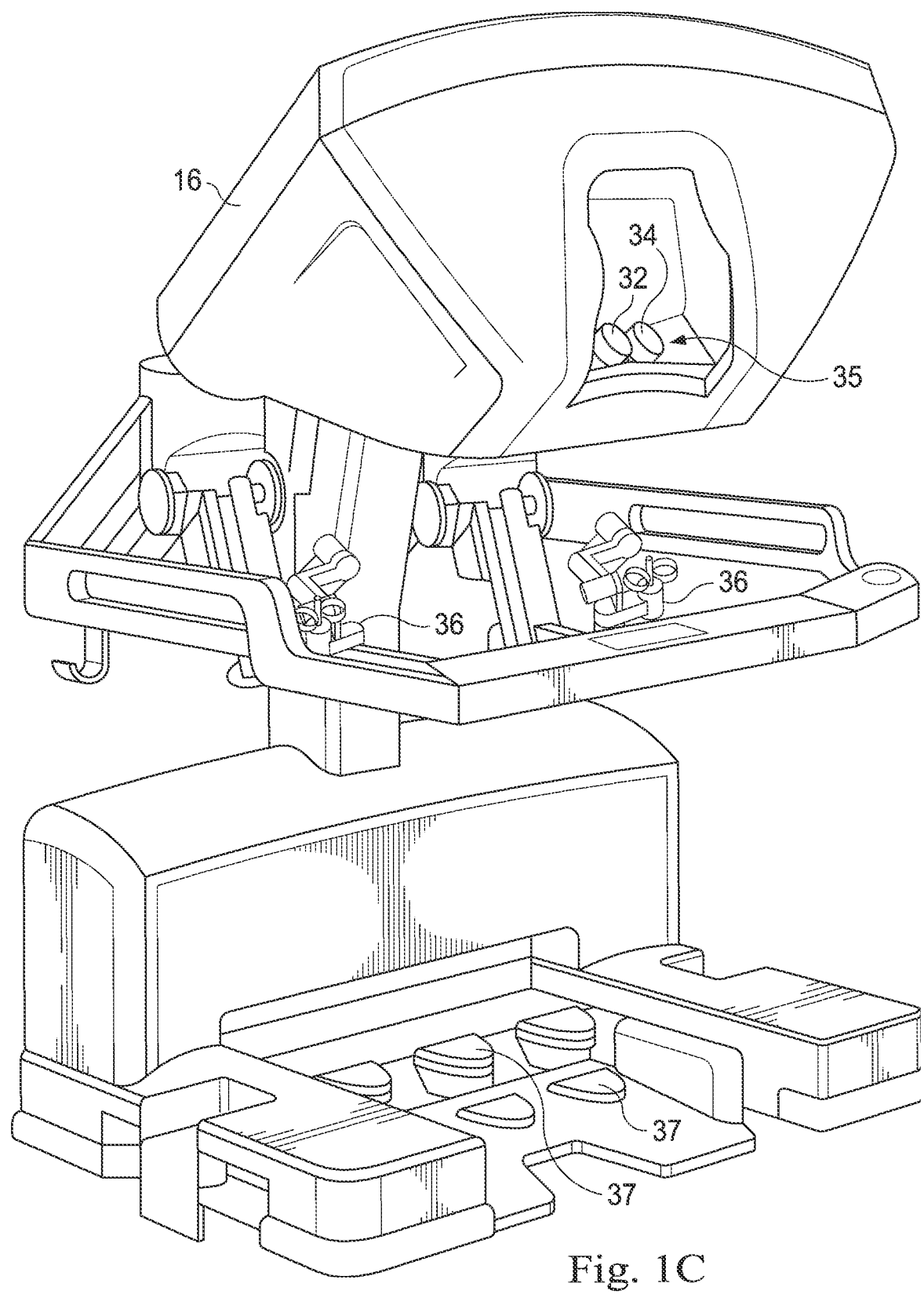
FIG. 1C is a perspective view of an operator input system according to some embodiments.

FIGS. 1A, 1B, and 1C together provide an overview of a medical system 10 that may be used in, for example, medical procedures including diagnostic, therapeutic, or surgical procedures. The medical system 10 is located in a medical environment 11. The medical environment 11 is depicted as an operating room in FIG. 1A. In other embodiments, the medical environment 11 may be an emergency room, a medical training environment, a medical laboratory, or some other type of environment in which any number of medical procedures or medical training procedures may take place. In still other embodiments, the medical environment 11 may include an operating room and a control area located outside of the operating room.

In one or more embodiments, the medical system 10 may be a teleoperational medical system that is under the teleoperational control of a surgeon. In alternative embodiments, the medical system 10 may be under the partial control of a computer programmed to perform the medical procedure or sub-procedure. In still other alternative embodiments, the medical system 10 may be a fully automated medical system that is under the full control of a computer programmed to perform the medical procedure or sub-procedure with the medical system 10. One example of the medical system 10 that may be used to implement the systems and techniques described in this disclosure is the da Vinci® Surgical System manufactured by Intuitive Surgical Operations, Inc. of Sunnyvale, California.

As shown in FIG. 1A, the medical system 10 generally includes an assembly 12, which may be mounted to or positioned near an operating table O on which a patient P is positioned. The assembly 12 may be referred to as a patient side cart, a surgical cart, or a surgical robot. In one or more embodiments, the assembly 12 may be a teleoperational assembly. The teleoperational assembly may be referred to as, for example, a manipulating system and/or a teleoperational arm cart. A medical instrument system 14 and an endoscopic imaging system 15 are operably coupled to the assembly 12. An operator input system 16 allows a surgeon S or other type of clinician to view images of or representing the surgical site and to control the operation of the medical instrument system 14 and/or the endoscopic imaging system 15.

The medical instrument system 14 may comprise one or more medical instruments. In embodiments in which the medical instrument system 14 comprises a plurality of medical instruments, the plurality of medical instruments may include multiple of the same medical instrument and/or multiple different medical instruments. Similarly, the endoscopic imaging system 15 may comprise one or more endoscopes. In the case of a plurality of endoscopes, the plurality of endoscopes may include multiple of the same endoscope and/or multiple different endoscopes.

The operator input system 16 may be located at a surgeon's control console, which may be located in the same room as operating table O. In one or more embodiments, the operator input system 16 may be referred to as a user control system. In some embodiments, the surgeon S and the operator input system 16 may be located in a different room or a completely different building from the patient P. The operator input system 16 generally includes one or more control device(s), which may be referred to as input control devices, for controlling the medical instrument system 14 or the imaging system 15. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and other types of input devices.

In some embodiments, the control device(s) will be provided with the same Cartesian degrees of freedom as the medical instrument(s) of the medical instrument system 14 to provide the surgeon S with telepresence, which is the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon S with telepresence. In some embodiments, the control device(s) are manual input devices that move with six degrees of freedom, and which may also include an actuatable handle for actuating instruments (for example, for closing grasping jaw end effectors, applying an electrical potential to an electrode, delivering a medicinal treatment, and actuating other types of instruments). Therefore, the degrees of freedom and actuation capabilities of the control device(s) are mapped to the degrees of freedom and range of motion available to the medical instrument(s).

The assembly 12 supports and manipulates the medical instrument system 14 while the surgeon S views the surgical site through the operator input system 16. An image of the surgical site may be obtained by the endoscopic imaging system 15, which may be manipulated by the assembly 12. The assembly 12 may comprise multiple endoscopic imaging systems 15 and may similarly comprise multiple medical instrument systems 14 as well. The number of medical instrument systems 14 used at one time will generally depend on the diagnostic or surgical procedure to be performed and on space constraints within the operating room, among other factors. The assembly 12 may include a kinematic structure of one or more non-servo controlled links (e.g., one or more links that may be manually positioned and locked in place, generally referred to as a manipulator support structure) and a manipulator. When the manipulator takes the form of a teleoperational manipulator, the assembly 12 is a teleoperational assembly. The assembly 12 includes a plurality of motors that drive inputs on the medical instrument system 14. In an embodiment, these motors move in response to commands from a control system (e.g., control system 20). The motors include drive systems which when coupled to the medical instrument system 14 may advance a medical instrument into a naturally or surgically created anatomical orifice. Other motorized drive systems may move the distal end of said medical instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors may be used to actuate an articulable end effector of the medical instrument for grasping tissue in the jaws of a biopsy device or the like. Medical instruments of the medical instrument system 14 may include end effectors having a single working member such as a scalpel, a blunt blade, an optical fiber, or an electrode. Other end effectors may include, for example, forceps, graspers, scissors, or clip appliers.

The medical system 10 also includes a control system 20. The control system 20 includes at least one memory 24 and at least one processor 22 (which may be part of a processing unit) for effecting control between the medical instrument system 14, the operator input system 16, and other auxiliary systems 26 which may include, for example, imaging systems, audio systems, fluid delivery systems, display systems, illumination systems, steering control systems, irrigation systems, and/or suction systems. A clinician may circulate within the medical environment 11 and may access, for example, the assembly 12 during a set up procedure or view a display of the auxiliary system 26 from the patient bedside. In some embodiments, the auxiliary system 26 may include a display screen that is separate from the operator input system 16. In some examples, the display screen may be a standalone screen that is capable of being moved around the medical environment 11. The display screen may be orientated such that the surgeon S and one or more other clinicians or assistants may simultaneously view the display screen.

Though depicted as being external to the assembly 12 in FIG. 1A, the control system 20 may, in some embodiments, be contained wholly within the assembly 12. The control system 20 also includes programmed instructions (e.g., stored on a non-transitory, computer-readable medium) to implement some or all of the methods described in accordance with aspects disclosed herein. While the control system 20 is shown as a single block in the simplified schematic of FIG. 1A, the control system 20 may include two or more data processing circuits with one portion of the processing optionally being performed on or adjacent the assembly 12, another portion of the processing being performed at the operator input system 16, and the like.

Any of a wide variety of centralized or distributed data processing architectures may be employed. Similarly, the programmed instructions may be implemented as a number of separate programs or subroutines, or they may be integrated into a number of other aspects of the systems described herein, including teleoperational systems. In one embodiment, the control system 20 supports wireless communication protocols such as Bluetooth, IrDA, HomeRF, IEEE 802.11, DECT, and Wireless Telemetry.

The control system 20 is in communication with a database 27 which may store one or more clinician profiles, a list of patients and patient profiles, a list of procedures to be performed on said patients, a list of clinicians scheduled to perform said procedures, other information, or combinations thereof. A clinician profile may comprise information about a clinician, including how long the clinician has worked in the medical field, the level of education attained by the clinician, the level of experience the clinician has with the medical system 10 (or similar systems), or any combination thereof. Additionally, the clinician profile may include information about a clinician's preferences regarding settings of the control system 20. These preferences may be stored in the database 27. In some embodiments, the stored preferences may indicate the clinician's preferred default configuration for the control system 20.

The database 27 may be stored in the memory 24 and may be dynamically updated. Additionally or alternatively, the database 27 may be stored on a device such as a server or a portable storage device that is accessible by the control system 20 via an internal network (e.g., a secured network of a medical facility or a teleoperational system provider) or an external network (e.g., the Internet). The database 27 may be distributed throughout two or more locations. For example, the database 27 may be present on multiple devices which may include the devices of different entities and/or a cloud server. Additionally or alternatively, the database 27 may be stored on a portable user-assigned device such as a computer, a mobile device, a smart phone, a laptop, an electronic badge, a tablet, a pager, and other similar user devices.

In some embodiments, the control system 20 may include one or more servo controllers that receive force and/or torque feedback from the medical instrument system 14. Responsive to the feedback, the servo controllers transmit signals to the operator input system 16. The servo controller(s) may also transmit signals instructing assembly 12 to move the medical instrument system(s) 14 and/or endoscopic imaging system 15 which extend into an internal surgical site within the patient, body via openings in the body. Any suitable conventional or specialized servo controller may be used. A servo controller may be separate from, or integrated with, assembly 12. In some embodiments, the servo controller and assembly 12 are provided as part of a teleoperational arm cart positioned adjacent to the patient's body.

The control system 20 can be coupled with the endoscopic imaging system 15 and can include a processor to process captured images for subsequent display, such as to a surgeon on the surgeon's control console, or on another suitable display located locally and/or remotely. For example, where a stereoscopic endoscope is used, the control system 20 can process the captured images to present the surgeon with coordinated stereo images of the surgical site as a field of view image. Such coordination can include alignment between the opposing images and can include adjusting the stereo working distance of the stereoscopic endoscope.

In alternative embodiments, the medical system 10 may include more than one assembly 12 and/or more than one operator input system 16. The exact number of assemblies 12 will depend on the surgical procedure and the space constraints within the operating room, among other factors. The operator input systems 16 may be collocated or they may be positioned in separate locations. Multiple operator input systems 16 allow more than one operator to control one or more assemblies 12 in various combinations. The medical system 10 may also be used to train and rehearse medical procedures.

FIG. 1B is a perspective view of one embodiment of an assembly 12 which may be referred to as a manipulating system, patient side cart, surgical cart, teleoperational arm cart, or surgical robot. The assembly 12 shown provides for the manipulation of three surgical tools 30a, 30b, and 30c (e.g., medical instrument systems 14) and an imaging device 28 (e.g., endoscopic imaging system 15), such as a stereoscopic endoscope used for the capture of images of the site of the procedure. The imaging device 28 may transmit signals over a cable 56 to the control system 20. Manipulation is provided by teleoperative mechanisms having a number of joints. The imaging device 28 and the surgical tools 30a-c can be positioned and manipulated through incisions in the patient so that a kinematic remote center is maintained at the incision to minimize the size of the incision. Images of the surgical site can include images of the distal ends of the surgical tools 30a-c when they are positioned within the field-of-view of the imaging device 28. The imaging device 28 and the surgical tools 30a-c may each be therapeutic, diagnostic, or imaging instruments.

FIG. 1C is a perspective view of an embodiment of the operator input system 16 at the surgeon's control console. The operator input system 16 includes a left eye display 32 and a right eye display 34 for presenting the surgeon S with a coordinated stereo view of the surgical environment that enables depth perception. The left and right eye displays 32, 34 may be components of a display system 35. In other embodiments, the display system 35 may include one or more other types of displays. In some embodiments, image(s) displayed on the display system 35 may be separately or concurrently displayed on at least one display screen of the auxiliary system 26.

The operator input system 16 further includes one or more input control devices 36, which in turn cause the assembly 12 to manipulate one or more instruments of the endoscopic imaging system 15 and/or the medical instrument system 14. The input control devices 36 can provide the same Cartesian degrees of freedom as their associated instruments to provide the surgeon S with telepresence, or the perception that the input control devices 36 are integral with said instruments so that the surgeon has a strong sense of directly controlling the instruments. Therefore, the degrees of freedom of each input control device 36 are mapped to the degrees of freedom of each input control device's 36 associated instruments (e.g., one or more of the instruments of the endoscopic imaging system 15 and/or the medical instrument system 14.). To this end, position, force, and tactile feedback sensors (not shown) may be employed to transmit position, force, and tactile sensations from the medical instruments, e.g., the surgical tools 30a-c or the imaging device 28, back to the surgeon's hands through the input control devices 36. Additionally, the arrangement of the medical instruments may be mapped to the arrangement of the surgeon's hands and the view from the surgeon's eyes so that the surgeon has a strong sense of directly controlling the instruments. Input control devices 37 are foot pedals that receive input from a user's foot. Aspects of the operator input system 16, the assembly 12, and the auxiliary systems 26 may be adjustable and customizable to meet the physical needs, skill level, or preferences of the surgeon S.

Figure 2:
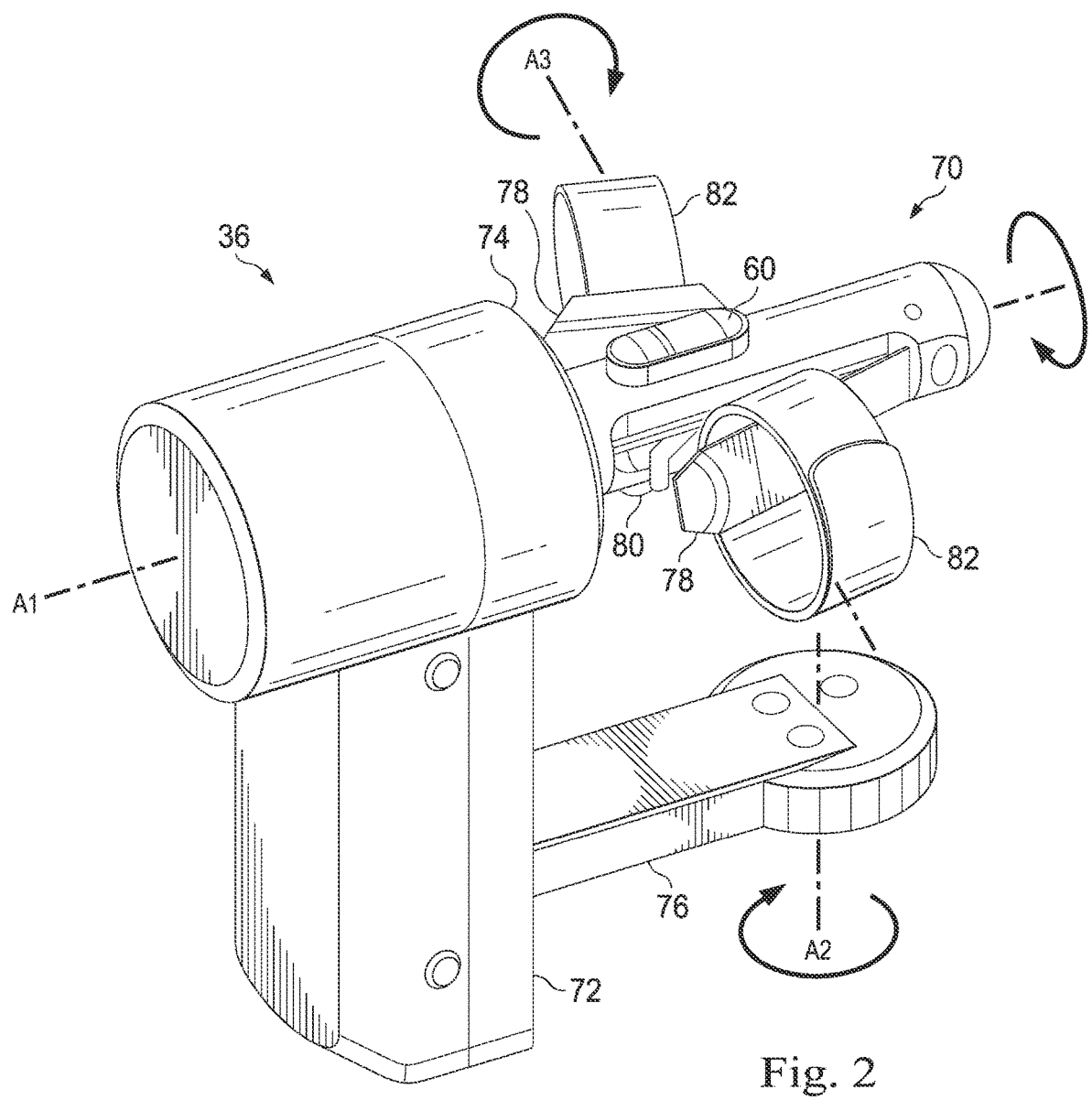
FIG. 2 is a perspective view of an input control device of an operator input system according to some embodiments.

With reference to FIG. 2, each input control device 36 includes a four degree of freedom gimbal or wrist that allows rotation of an actuatable handle 70 about three axes axis— A1, axis A2, and axis A3. In several examples, the operator input system 16 includes one or more joints and/or links that facilitate the rotation of the handle 70 about axis A1, axis A2, and axis A3. The handle 70 is coupled to a first elbow-shaped link 72 by a first rotatable joint 74 that permits continuous rotation of the handle. The first link 72 is coupled to a platform 76. Each input control device 36 will generally allow movement of the handle 70 within the workspace control workspace with a plurality of degrees of freedom, typically with six degrees of freedom, three rotational degrees of freedom and three translational degrees of freedom. This allows the actuatable handle 70 to be moved to any position and any orientation within its range of motion. The actuatable handle 70 includes grip actuators 78 and/or switches 60, 80 to allow the operator to actuate the instruments 30a-c or 28 being positioned by the motion of the handle. Finger loops 82 are attached to the handle 70 to prevent the operator's fingers from slipping on the handle.

The operator input system 16 provides a "head-in" graphical user interface which allows the surgeon to perform a variety of functions with the medical instruments while his or her head remains in the operator input system 16 with eyes viewing the displays 32, 34 and with hands remain engaged with the input control devices 36. As features and interaction modalities of the teleoperational system and medical instruments increase, it becomes impracticable to continue to add additional physical input control devices (e.g., foot pedals, switches, buttons) for each additional feature. Including graphical menus in the user interface provide a rich, extensible platform to access instrument and system capabilities without adding additional physical user inputs.

During a surgical procedure, the medical system 10 may function in an instrument control mode or a "following" operational mode in which the movement of an instrument in the surgical environment 100 follows the movements of the user's hand in the input control device 36 associated with the instrument. In the instrument control mode, the control device may move with as many as six degrees of freedom to control movement of the instrument in the surgical environment in a corresponding six degrees of freedom. In some embodiments, an operator (e.g., surgeon S) may exit the instrument control mode and transfer into a graphical user interface mode or menu mode in which additional functions of the instruments or medical system are accessible by a graphical menu. In the graphical user interface mode, the movement of the input control device 36 may be constrained to motion in translational directions that correspond to the directional arrangement of menu options in the graphical menu. In the graphical user interface mode, the operator is not required to move his or her hands very far from a starting position of the input control devices 36 (i.e., the position of the input control devices 36 when the operator enters the graphical user interface mode). Additionally, in the graphical user interface mode, the operator may actuate one or more menu options by simply moving an input control device 36 in one or more of the translational directions that correspond to the directional arrangement of menu options in the graphical menu. This may allow the operator to interact with the menu options without having to open his or her grip on the grip actuators 78 of the input control device 36. Further, because the movement of the input control device 36 is constrained to motion in translational directions, the movements needed to interact with the graphical menu may be made regardless of the orientation of the operator's hands. This provides a more seamless transition between the instrument control mode and the graphical user interface mode. Furthermore, the graphical user interface mode helps reduce on-screen clutter in an image 102 of a field of view of a surgical environment 100 within the patient P. In this way, some messages may be presented to the surgeon S only when the graphical user interface mode is activated. In addition, because the movement of the input control device 36 is constrained to motion in translational directions, the surgeon S may interact quickly with the graphical menu after learning the movement patterns corresponding to certain interactions, such as taking a photo of the surgical environment 100. The surgeon S may also discover new movement patterns and interactions with the graphical menu by slowly navigating the graphical menu to discover what options are available.

Figure 3:
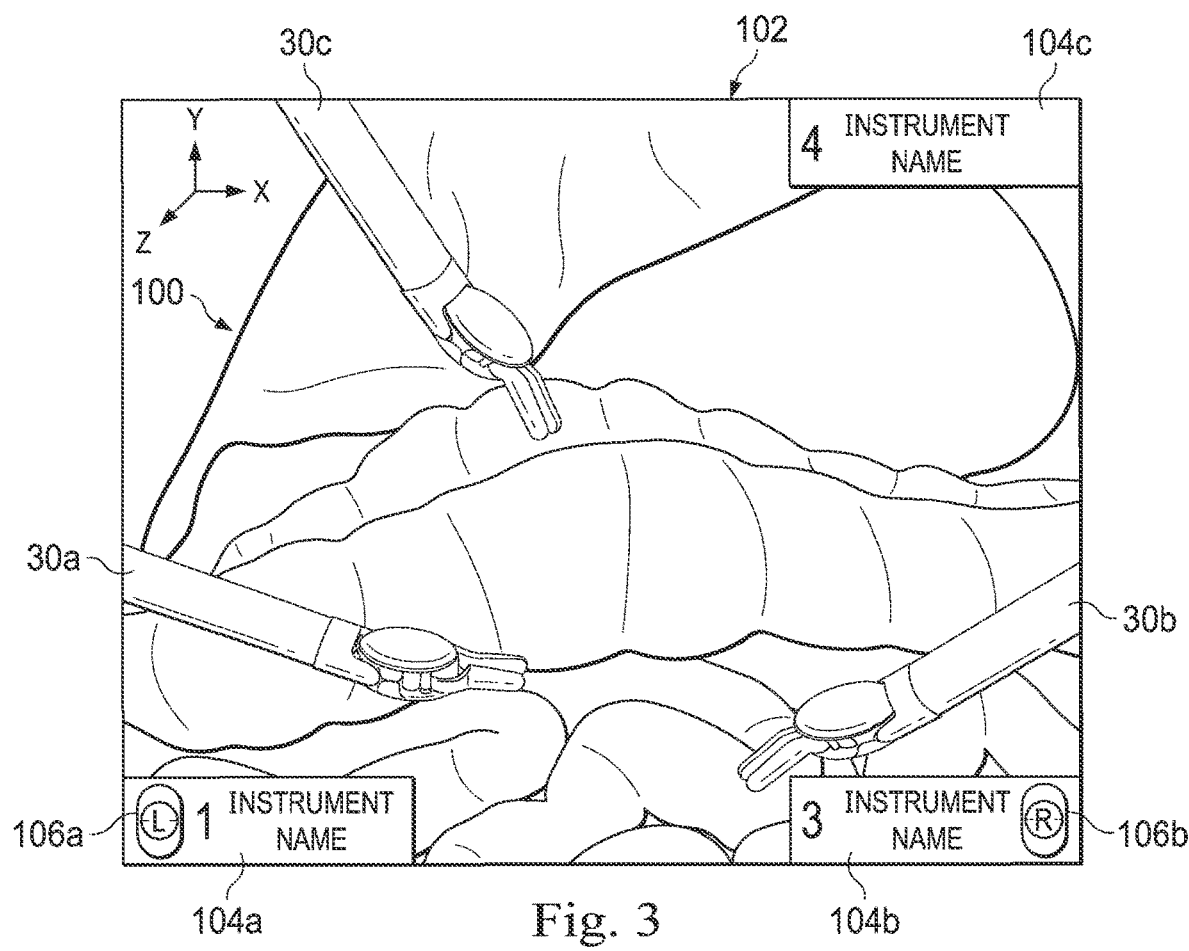
FIG. 3 is a field of view of a surgical environment with a graphical menu overlaid on the field of view according to some embodiments.

FIG. 3 illustrates the image 102 of the field of view of the surgical environment 100 within the patient P that may be generated when the medical system 10 is in the menu mode. The image 102 may be associated with an X, Y, Z cartesian coordinate system. The image 102 may be generated by an imaging instrument, such as imaging instrument 28. The image 102 may be a three-dimensional image obtained by a stereoscopic endoscope and generated as a composite image of the images visible to a user through right and left eye displays (e.g., displays 32, 34 in FIG. 1C). The image 102 of the field of view includes a distal end portion of instrument 30a, a distal end portion of instrument 30b, and a distal end portion of instrument 30c. The image 102 also includes information fields 104a, 104b, and 104c which may include instructions to the clinician, warnings, instrument identification information, status information, or other information relevant to the surgical procedure.

As shown in FIG. 3, the information fields 104a, 104b, 1.04c include instrument identification information. In that regard, the information field 104a corresponds to instrument 30a and includes the name of instrument 30a, such as "forceps," "graspers," "scissors," or "clip appliers," depending on the type of instrument being used as instrument 30a. Similarly, the information field 104b corresponds to instrument 30b and includes the name of instrument 30b, which may be any of the names listed above with respect to instrument 30a. Further, the information field 104c corresponds to instrument 30c and includes the name of instrument 30c, which may be any of the names listed above with respect to instrument 30a. In several embodiments, the information fields 104a, 104b, 104c are displayed around the periphery of the field of view of the surgical environment 100, for example, in respective corners of the image 102. The information fields 104a, 104h, 104c may be superimposed over the field of view of the surgical environment 100 or may be outside the field of view, bordering a peripheral edge of the field of view. Additionally or alternatively, the information fields 104a, 104b, 104c may be displayed in close proximity to the instruments 30a, 30b, 30c to which the information fields 104a, 104b, 104c respectively correspond. In alternative embodiments, the information fields 104a, 104b, 104c may be displayed along a same peripheral edge of the image 102 (e.g., along the bottom edge, the left edge, the right edge, or the top edge).

In some embodiments, the image 102 may optionally include directional icons 106a, 106b. The directional icons 106a, 106b may be superimposed over or included within the information field to which each directional icon corresponds. For example, the directional icon 106a corresponds to the information field 104a and thus corresponds to the instrument 30a. Therefore, the directional icon 106a may be superimposed over or included within the information field 104a, as shown in the embodiment of FIG. 3. Similarly, the directional icon 106b corresponds to the information field 104b and thus corresponds to the instrument 30b. As shown in the embodiment of FIG. 3, the directional icon 106b may be superimposed over or included within the information field 104b. The directional icons indicate the directions in which the user (e.g., the surgeon S) may move the input control devices 36 in the graphical user interface mode.

In the embodiment shown in FIG. 3, the directional icon 106a includes the letter "L" indicating that the left input control device 36 will control display and selection in a menu associated with the information field 104a. The directional icon 106a also includes an oval elongated along the Y-axis indicating that the left input control device 36 is constrained to translational motion in a direction associated with the Y-axis. The directional icon 106b includes the letter "R" indicating that the right input control device 36 will control display and selection in a menu associated with the information field 104b. The directional icon 106b also includes an oval elongated along the Y-axis indicating that the right input control device 36 is constrained to translational motion in a direction associated with the Y-axis.

In some examples, translational movement along the axis A2 (FIG. 2) in the input control device 36 space may coordinate with translational motion in the Y-direction (e.g., up/down) in the image 102 space. Similarly, translational movement along the axis A3 (FIG. 2) in the input control device 36 space may coordinate with translational motion in the X-direction (e.g., right/left) in the image 102 space. Additionally, translational movement along the axis A1 (FIG. 2) in the input control device 36 space may coordinate with translational motion in the Z-direction (e.g., in/out) in the image 102 space.

The position of the input control devices 36 when the teleoperational assembly 12 enters the menu mode from the instrument control mode, which may be referred to as a non-menu mode, is considered to be a neutral position of the input control devices 36. The neutral position may also be referred to as a starting position. As discussed in greater detail below, when the teleoperational assembly 12 transitions from the menu mode back to the non-menu mode, the input control devices 36 are in the neutral position (i.e., the same location and orientation that they were in when the teleoperational assembly 12 entered the menu mode).

As shown in FIG. 3, information fields are shown for each instrument 30a, 30b, 30c, In some embodiments, though, information fields are only shown for the instruments that were "active" (i.e., being controlled by the surgeon S) when the teleoperational assembly 12 entered the menu mode. For example, if the surgeon S was controlling instruments 30a and 30b when the teleoperational assembly 12 entered the menu mode, only the information fields 104a, 104b would be provided in the image 102. In another example, if the surgeon S was controlling instruments 30a and 30c when the teleoperational assembly 12 entered the menu mode, only the information fields 104a, 104c would be provided in the image 102.

In some embodiments, when the teleoperational assembly 12 enters the menu mode, the directional icons 106a, 106b are shown in the image 102. In some embodiments, directional icons are only shown for the instruments that were "active" when the teleoperational assembly 12 entered the menu mode. For example, if the surgeon S was controlling instruments 30a and 30b when the teleoperational assembly 12 entered the menu mode, only the directional icons 106a, 106b would be provided in the image 102. In another example, if the surgeon S was controlling instruments 30a and 30c when the teleoperational assembly 12 entered the menu mode, only the directional icon 106a and a directional icon corresponding to the instrument 30c would be provided in the image 102.

In some embodiments, to activate a graphical menu associated with the instrument 30b and actuated by the right input control device 36, the user moves the input control device 36 in a translational direction corresponding to the +Y-direction in the image 102 space. For exemplary purposes only and for the sake of clarity, the discussion below will take place with respect to the graphical menu associated with the instrument 30b. It is to be understood that the discussion also applies to a graphical menu associated with the instrument 30a and/or with a graphical menu associated with the instrument 30c.

A haptic force may provide a "click" sensation through the right input control device 36 to provide confirmation of the launch of the menu. The haptic force may also be referred to as a haptic feedback. As further confirmation of the launch of the menu. The menu will appear on the image 102 after the surgeon S moves the input control device 36 in the direction corresponding to the +Y-axis in the image 102 space. After the application of the haptic force, the input control device 36 may return or "snap back" to the neutral position. Even though the input control device 36 "snaps back" to the neutral position, the menu may remain visible on the image 102. The return to the neutral position allows minimal deviation of the pose of the surgeon's hand to provide for better ergonomics (e.g., the surgeon's arm and/or wrist is not required to excessively deviate from the neutral position). This re-centering of the input control device 36 also allows reentry into the non-menu mode to proceed more quickly. Additionally, the re-centering of the input control device 36 preserves the surgeon's hand-eye arrangement when entering and exiting the menu mode.

Figure 4:
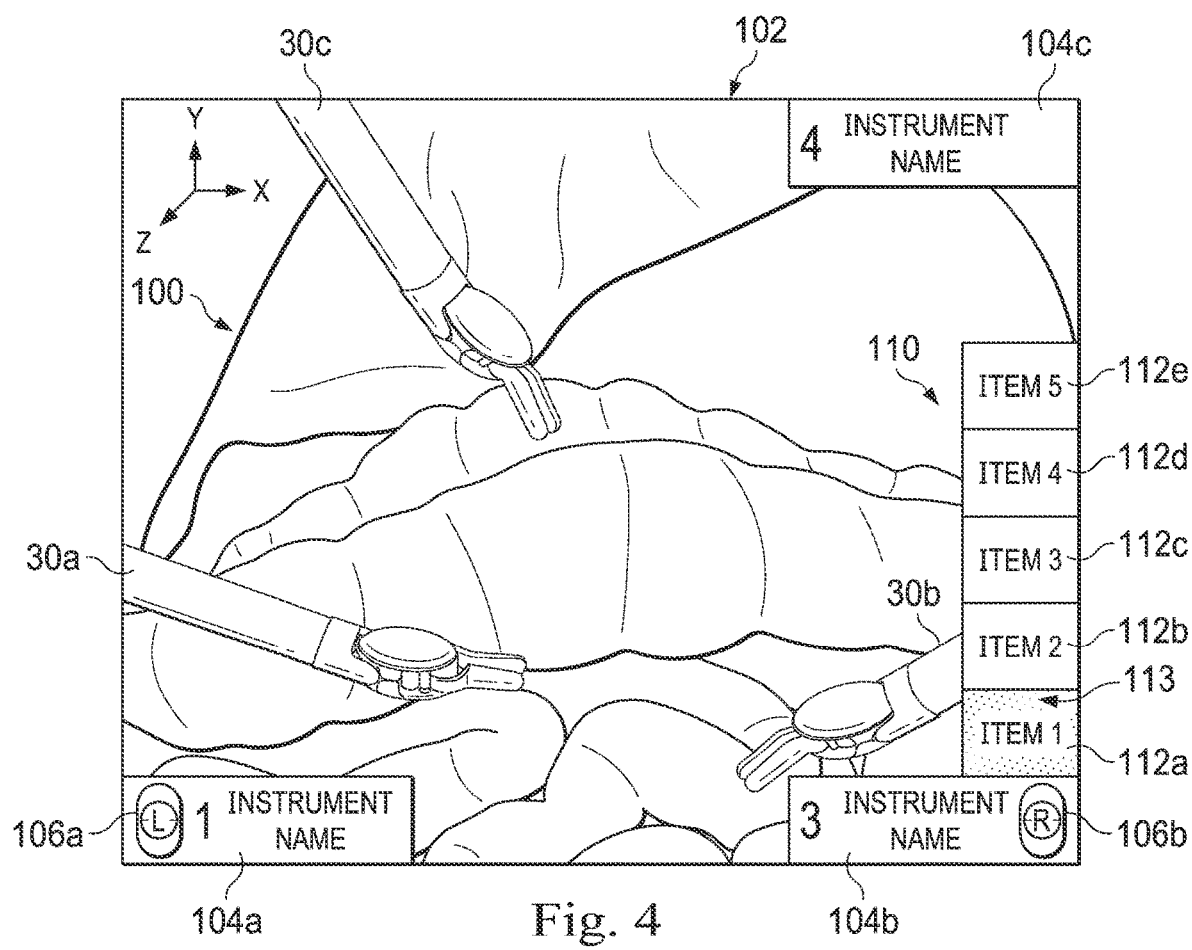
FIG. 4 is a field of view of a surgical environment with an expanded graphical menu overlaid on the field of view according to some embodiments.

As shown in FIG. 4, the graphical menu 110 corresponding to the instrument 30b and/or associated with the right input control device 36 is activated and is superimposed on the image 102. Through the graphical menu 110, the user may access features and capabilities of the instrument 301 or of the medical system 10. The graphical menu 110 includes a set of directionally arranged menu options 112a-112e. In this embodiment, the menu options 112a-112e are arranged linearly in a +Y-direction extending from the information field 104b. As seen in FIG. 4, the graphical menu 110 and the menu options 112a-112e are located along the periphery of the image 102. The location of the menu 110 allows the surgeon S to easily determine that instrument-specific menu options 112a-112e of the graphical menu 110 correspond to the instrument 30b. In some embodiments, the default location of the graphical menu 110 is along the periphery of the image 102 extending from the information field 104b, as shown in FIG. 4. In other embodiments, such as embodiments where the information field 104b is not displayed along the periphery of the image 102, the graphical menu 110 may be displayed as extending from the information field 104b but may not be located along the periphery of the image 102. The location of the graphical menu 110 may therefore depend on the location of the information field 104b. Superimposing the graphical menu 110 on the image 102 allows the surgeon to access features of the instrument 30b while remaining focused on the surgical environment.

In the embodiment of FIG. 4, the menu options 112a-112e may include icons or text associated with a selectable function of the instrument 30b or the medical system 10. A cursor 113 is a movable indicator that indicates a current location within the menu 110. The current location of the cursor 113 may be referred to as a control location. Movement of the cursor 113 may be directionally constrained by the direction of the menu options and the corresponding constraint on the input control device 36. The cursor may be context-dependent in the sense that control options available for access with the cursor are dependent on the cursor's location within the menu 110. The cursor 113 may be a highlight on one of the menu options 112a-112e as shown in FIG. 4. In other embodiments, the cursor may be an outline around a menu option, a differently colored menu option, a differently shaded menu option, a differently patterned menu option, or any other graphical indicator of a current location within the menu. In some embodiments, movement of the cursor 113 to a menu option 112a-112e causes the menu option to become selected. In other embodiments, an additional movement of the instrument 30b or activation of a switch 60 or 80 may be required to cause the menu option to become selected. In some embodiments, a selected menu option may be indicated by the location of the cursor 113. In the embodiment shown in FIG. 4, the cursor 113 is currently located on menu option 112a, indicating that a function associated with menu option 112a is selected. The non-selected menu options 112b, 112c, 112d, 112e are not highlighted. In some embodiments, when the graphical menu 110 is activated, one menu option is automatically selected. For example, menu option 112a, the menu option located closest to the information field 104b, may be automatically selected. Because the menu option 112a is the first menu option above the information field 104b1, when the user moves the input control device 36 in a +Y-direction to activate the menu 110, the cursor 113 automatically moves to the first menu option of the menu 110, i.e menu option 112a. In other embodiments, any one of the menu options 112a-112e is automatically selected when the menu 110 is activated. In still other embodiments, when the graphical menu 110 is activated, the cursor 113 is located on the information field 104b, and a motion of the input control device 36 (e.g., in a +Y-direction) is needed to move the cursor 113 and select a menu option (e.g., menu option 112a).

Each menu option may have different options available to be selected or manipulated by the surgeon S, where each option controls a feature of the medical system 10 or a feature of the instrument to which the menu 110 corresponds. For example, when the menu 110 is activated using the input control device 36 associated with the instrument 301, the menu options may correspond to the available features of the instrument 301. When the menu 110 is activated using the input control device 36 associated with the instrument 30a, the menu options may correspond to the available features of the instrument 30a. Similarly, when the menu 110 is activated using the input control device 36 associated with the instrument 30c, the menu options may correspond to the available features of the instrument 30c. The available options in each menu may be different depending on the type of instruments being used. For example, if the instrument 30a is a different instrument than the instrument 30b, the menu options associated with the instrument 30a may be different than the menu options associated with the instrument 30b. In other examples, though, the menu options may be the same for each instrument 30a, 30b, 30c.

In some embodiments, only one menu 110 is displayed in the image 102 at one time. Thus, if the menu 110 corresponding to the instrument 30b is active, the surgeon S must deactivate that menu if the surgeon S wants to activate the menu 110 corresponding to the instrument 30a. To deactivate the menu 110 corresponding to the instrument 30b, the surgeon S may move the right input control device 36 in a direction corresponding to the −Y-direction in the image 102 space (i.e., down) when the menu option 112a is selected. Then, to activate the menu 110 corresponding to the instrument 30a, the surgeon S may move the left input control device 36 in a direction corresponding to the +Y-direction in the image 102 space (i.e., up). In alternative embodiments, more than one menu 110 may be displayed on the image 102 at one time.

The embodiments described above have generally been made with reference to the input control device 36 corresponding to the instrument 30b being moved to navigate the menu 110 corresponding to the instrument 30b. In other embodiments, the input control device 36 corresponding to the instrument 30a may be used to navigate the menu 110 corresponding to the instrument 30b. In further embodiments, each input control device 36 may be used interchangeably to navigate the menu 110. In various alternative embodiments, more than one graphical menu may be displayed on the image 102. For example, a menu corresponding to the instrument 30a and a second menu corresponding to the instrument 30b may each be displayed on the image 102. In such embodiments, the menu corresponding to the instrument 30a may be navigated by movements of the input control device 36 corresponding to the instrument 30a. Similarly, the menu corresponding to the instrument 30b may be navigated by movements of the input control device 36 corresponding to the instrument 30b.

Figure 5:
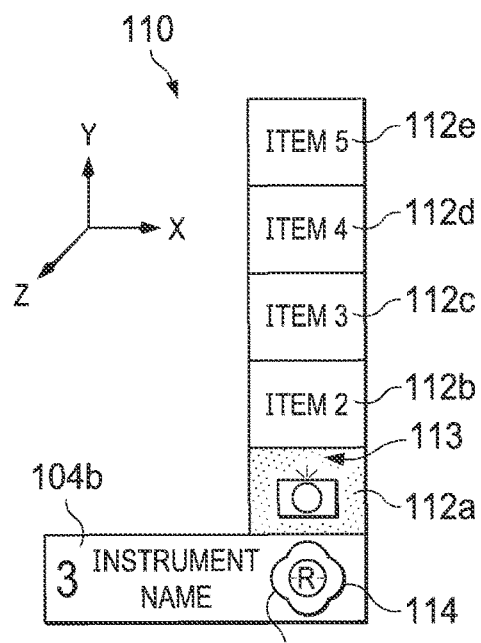
FIG. 5 is an expanded graphical menu with a first menu option selected according to some embodiments.

In the embodiment shown in FIG. 5, the graphical menu 110 is activated, and the menu option 112a is selected. For purposes of clarity, FIG. 5 only illustrates the information field 104b and the menu 110. It is to be understood that the remaining components of the image 102, including but not limited to the distal ends of the instruments 30a, 30b, 30c, the other information fields 104a, 104c, and the patient anatomy do not change while the surgeon S interacts with the menu 110. As shown in FIG. 5, in one embodiment, the menu option 112a includes a camera icon, indicating an image capture function of the menu option 112a. Selecting the menu option 112a may initiate capture of a photo of the surgical site.

In this embodiment, when the cursor 113 is on the menu option 112a, the right input control device 36 is constrained to move in translational directions based on the current location of the cursor 113. More specifically, movement of the right input control device 36 may be constrained to the two degrees of translational freedom associated with the X and Y-directions in the image 102 space. For example, movement of the right input control device 36 in the direction corresponding to the +Y-direction may move the cursor 113 to the menu option 112b. Movement of the right input control device 36 in the direction corresponding to the −Y-direction may close the menu 110, hiding the menu options 112a-112e from view. Movement of the right input control device 36 to the right or left (i.e., in the direction corresponding to +/−X-direction in the image 102 space) may select a directionally arranged secondary menu option for actuating the camera to capture an image of the surgical environment. In some embodiments, the directionally arranged secondary menu options for a selected menu option may be graphically displayed (see FIG. 6A). In other embodiments, as in FIG. 5 where there is a single secondary menu option for the selected menu option 112a, the directionally arranged secondary menu option (e.g., activate the camera) may not be graphically displayed. In some embodiments, when the right input control device 36 is moved to advance the cursor 113, close the menu 110, or actuate the camera, a haptic force provides a "click" sensation to the user controlling the right input control device 36 to provide confirmation of the action. After the corresponding haptic force is delivered, the input control device 36 may return or "snap back" to a neutral position. In other embodiments, the menu option 112a, for example, may additionally be actuated if the surgeon S presses the switch 80 on the input control device 36 to capture the image. In alternative embodiments, the menu option 112a may be actuated by moving the input control device 36 forward in the Z-direction (i.e., along the axis A1 in FIG. 2) to capture the image. In further alternative embodiments, the menu option 112a may be actuated by opening and/or closing the grip actuators 78 of the input control device 36. In further embodiments, the menu option 112a may be actuated when a gestural input is detected. For example, the control system 20 may detect a gestural input (e.g., hand motion, arm motion, foot motion, leg motion, head motion, etc.) of the surgeon S. Further, the menu option 112a may be actuated using any combination of one or more of the above inputs.

In some embodiments, the constraint on the input control device 36 when the cursor is located at the menu option 112a is illustrated by a directional icon 114, which includes the letter "R" indicating control by the right input control device 36 and a cross-shaped FIG. 116 indicating that the right input control device 36 may be constrained to motion in directions corresponding to the X and Y-directions in the image 102 space. As shown in FIG. 5, the directional icon 114 is superimposed over or included within the information field 104b. In such embodiments, the directional icon 114 would replace the directional icon 106b shown in FIG. 3. In other embodiments, the directional icon 114 may be placed to the left of the menu option 112a. In additional examples, the directional icon 114 may be placed in any other location in the image 102, such as above the menu 110, adjacent the distal end of the instrument 30b, etc.

In some embodiments, one or more of the menu options 112a-112e may include a subset of secondary menu options. The secondary menu options may become visible and thus selectable when the primary menu option 112a, 112b, 112c, 112d, 112e is selected. For example, in the embodiment shown in FIG. 6A, the primary menu option 112b includes secondary menu options 118, 119, and 120. The secondary menu options 118, 119, and 120 indicate different energy modes available for the instrument 30b. To navigate the cursor 113 from the primary menu option 112a to the primary menu option 112b, the right input control device 36 is moved in the direction corresponding to the +Y-direction in the image 102 space. As discussed above with respect to FIG. 5, when the cursor 113 is moved to the primary menu option 112b, a haptic force may provide a "click" sensation to the user through the right input control device 36. Then, the input control device 36 may return or "snap back" to the neutral position.

Figure 6A:
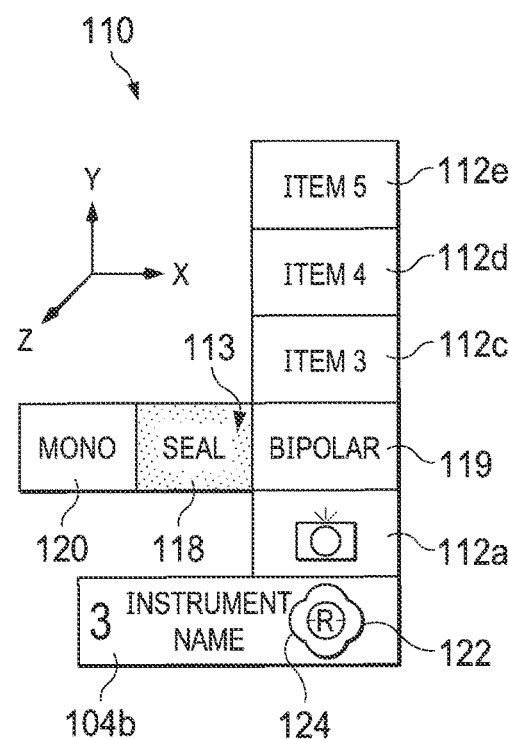
FIG. 6A is an expanded graphical menu with a second menu option selected according to some embodiments.
Figure 6B:
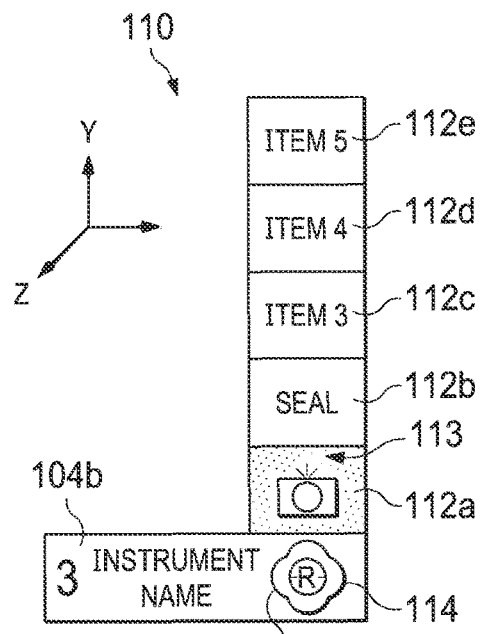
FIG. 6B is an expanded graphical menu with a first menu option selected after a second menu option has been changed according to some embodiments.

As shown in FIG. 6A, the graphical menu 110 is activated and a primary menu option 112b for choosing an energy mode of the instrument 30b is selected, revealing the three secondary menu options directionally arranged linearly in an X-direction and corresponding to three different energy modes: "bipolar" (menu option 119), "seal" (menu option 118), and "mono" (menu option 120). The instrument 30b may include one, some, or all of the above energy modes. In some embodiments, if a primary menu option includes secondary menu options (e.g., different energy modes), the secondary menu options automatically appear in the image 102 when the cursor 113 is moved to the primary menu option and the primary menu option is selected. For example, when the primary menu option 112b is selected, the secondary menu options 118, 119, and 120 are automatically shown in the image 102. In other embodiments, the secondary menu options 118, 119, and 120 may only be shown if the input control device 36 is moved in a direction corresponding to the -X-direction after the primary menu option 112b is selected. In some embodiments the primary menu option 112b and the secondary menu option 119 may be the same option or may be located in the same location in the image 102.

As shown in FIG. 6A, the cursor 113 is positioned on the secondary menu option 118, indicating selection of the secondary menu option 118. The cursor 113 may be moved in the X and Y-directions, and a haptic force may be provided, in the manner discussed above with respect to FIG. 5.

When the secondary menu option 118 is selected, movement of the input control device 36 is constrained to directional motion associated with X and Y-directional motion in the image 102 space. This constraint is depicted by the directional icon 122, which includes the letter "R" indicating control by the right input control device 36 and a cross-shaped FIG. 124 indicating that the right input control device 36 may be constrained to motion in directions corresponding to the X and Y-directions in the image 102 space. As shown in FIG. 6A, the directional icon 122 is superimposed over or included within the information field 104b. In such embodiments, the directional icon 122 would replace the directional icon 106b shown in FIG. 3. In other embodiments, the directional icon 122 may be placed to the left of the secondary menu option 120. In additional examples, the directional icon 122 may be placed in any other location in the image 102, such as above the secondary menu option 118, above the menu 110, adjacent the distal end of the instrument 30b, etc.

In some embodiments, the selection of the "seal" menu option 118 may be locked by moving the input control device 36 in a constrained direction corresponding the +Y or −Y-direction in the image 102 space. For example, FIG. 69 illustrates the graphical menu 110 after the menu option 112b has been set to "seal" and the input control device 36 has been moved in a constrained direction corresponding to the −Y-direction (e.g., down) in the image 102 space. The movement of the control device 36 has also returned the cursor 113 to the menu option 112a. In other embodiments the selection of the "seal" menu option 118 may be locked by exiting the menu mode while the menu option 118 is selected. The discussion above with respect to selecting the secondary menu option 118 also applies to selecting the secondary menu option 120. If the secondary menu option 118 is selected, the cursor 113 may be moved to the left e.g., the −X-direction) to select the secondary menu option 120.

Figure 7:
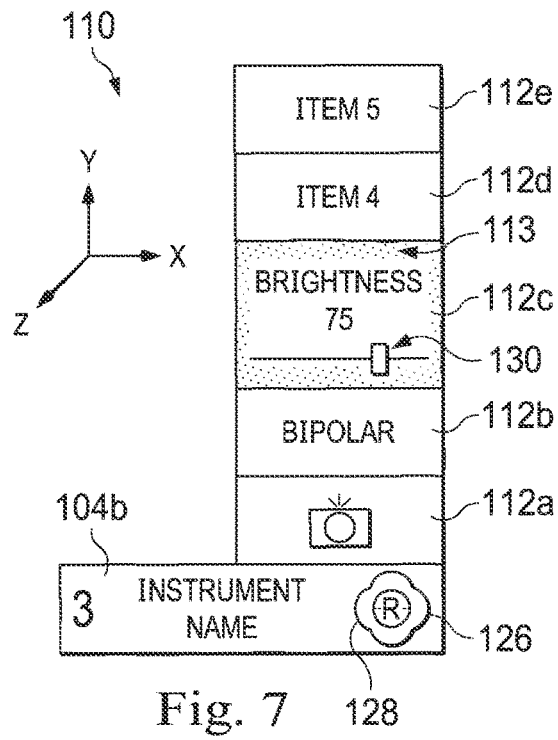
FIG. 7 is an expanded graphical menu with a third menu option selected according to some embodiments.

As shown in FIG. 7, the graphical menu 110 is activated, the cursor 113 is moved to the primary menu option 112c, and the primary menu option 112c is selected. In some embodiments, the primary menu option 112c corresponds to an adjustable parameter, such as brightness of the image 102. For example, the brightness of the image 102 may be controlled by adjusting an endoluminal light source associated with the endoscopic imaging system 15. To reach the menu option 112c, the right input control device 36 is moved in a direction corresponding to the +Y-direction in the image 102 space, as described above with respect to FIG. 5. If the menu option 112a is selected, and the surgeon S then wants to select the menu option 112c, the constrained right input control device 36 is translated in a direction corresponding to the +Y-direction in the image 102 space to move the cursor 113 up once to select the menu option 112b and then up a second time to select the menu option 112c. After each upward movement, a haptic force provides a "click" sensation through the input control device 36, and the input control device 36 "snaps back" to the neutral position.

In this embodiment, when the menu option 112c is selected, a slider bar 130 is displayed in the menu option 112c. In other embodiments, the slider bar 130 may be shown in the menu option 112c whenever the menu 110 is displayed. The slider bar 130 may move along a series of directionally arranged secondary menu options corresponding to a linear range of brightness levels. Movement of the slider bar 130 may correspond to constrained movement of the right input control device 36 in a translational direction corresponding to the +/−X-direction in the image 102 space. In some examples, each movement of the slider bar 130 in the left or right direction adjusts the brightness level by 5 units. For example, as shown in FIG. 7, the current brightness of the image 102 is set at level "75." If the input control device 36 is moved one time to the left, the brightness would be adjusted down to level "70." If the input control device 36 is moved one time to the right, the brightness would be adjusted up to level "80."

In other embodiments, each movement of the slider bar 130 in the left or right direction adjusts the brightness by 1 unit. Other examples may include different increments (e.g., 2 units, 3 units, 10 units, etc.) In further embodiments, if the surgeon S moves and holds the input control device 36 in a direction (e.g., left) corresponding to the −X-direction in the image 102 space, without letting the input control device 36 return to the neutral position, the brightness may continuously decrease until the input control device 36 is released and allowed to "snap back" to the neutral position. Similar continuous adjustments may be made to increase brightness by moving and holding the input control device 36 in a direction (e.g., right) corresponding to the +X-direction in the image 102 space and allowing the input control device 36 to "snap back" to the neutral position when the desired brightness has been reached.

In some embodiments, after each movement of the slider bar 130 in the left and right directions, a haptic force provides a "click" sensation through the input control device 36 to provide confirmation of the movement. After the input control device 36 is translated and the corresponding haptic force is applied, the input control device 36 may return or "snap back" to the neutral position.

In the embodiment shown in FIG. 7, a directional icon 126, indicates that the input control device 36 is constrained to move in a direction corresponding to the +/−X-direction in the image 102 space to move the slider bar 130 left and right and is constrained to move in a direction corresponding to the +/−Y-direction to move the cursor to up toward the menu option 112d or down toward the menu option 112b. As shown in FIG. 7, the directional icon 126 is superimposed on or placed within the information field 104. In such embodiments, the directional icon 126 would replace the directional icon 106b shown in FIG. 3. In other embodiments, the directional icon 126 may be placed in any other location in the image 102, such as above the menu 110, to the left of the menu option 112c, adjacent the distal end of the instrument 30b, etc.

In some embodiments, the surgeon S may activate a menu (not shown) for the instrument 30c from the menu 110 corresponding to the instrument 30b. In such examples, the input control device 36 is translated to move the cursor 113 up to select the menu option 112d and then up again to select the menu option 112e. When the menu option 112e is selected, further translational movement of the input control device 36 in the same direction (e.g., up) deactivates the menu 110 corresponding to the instrument 30b and activates the menu corresponding to the instrument 30c. The menu corresponding to the instrument 30c may be activated if the instrument 30c was "active" when the teleoperational assembly 12 entered the menu mode. In other examples, the menu corresponding to the instrument 30c may be activated even if the instrument 30c was not "active" when the teleoperational assembly 12 entered the menu mode.

In the embodiments discussed above, after each movement of the input control device 36 in any direction, a haptic force providing a "click" sensation will be provided to the surgeon S through the input control device 36 to provide confirmation of the movement. After the input control device 36 is moved and the corresponding haptic force is applied, the input control device 36 returns or "snaps back" to the neutral position. In alternative embodiments, the input control device 36 may be moved as many times and in as many directions as needed, within the constraints provided by the directionally arranged menu options, to reach a desired menu option and/or to perform a desired function. These movements may be made without the input control device 36 being "snapped back" to the neutral position after each individual movement. Instead, the input control device 36 may be "snapped back" to the neutral position after the entire sequence of movements has been completed.

For example, if the surgeon S wants to activate the menu 110 and adjust the brightness level from "75" to "85," the surgeon S may move the input control device 36 up the translational direction corresponding to the +Y-direction in the image 102 space) to activate the menu 110, up again to move from the menu option 112a to the menu option 112b, up again to move from the menu option 112b to the menu option 112c, right (e.g., the translational direction corresponding to the +X-direction in the image 102 space) to change the brightness from "75" to "80," and right again to change the brightness from "80" to "85." Thus, the input control device 36 will have followed an up-up-up-right-right movement path. After all of these movements have been made, then the input control device 36 may be "snapped back" to the neutral position. In some embodiments, haptic threes move the input control device 36 back to the neutral position following the same path, but in the reverse directions, from the movements the input control device 36 just made. For example, if the input control device followed an up-up-up-right-right movement path, then the haptic forces may move the input control device 36 back to the neutral position along a left-left-down-down-down movement path. In other embodiments, the haptic forces may return the input control device 36 back to the neutral position along the shortest straight-line path between the neutral position and the current position of the input control device 36.

Figure 8A:
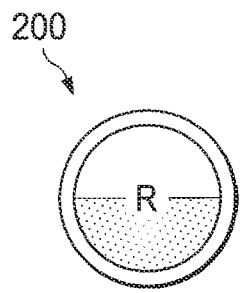
FIGS. 8A-8D are directional icons for an input control device according to some embodiments.

FIGS. 8A-8D illustrate directional icons for an input control device according to some embodiments. FIGS. 9A-9C illustrate additional directional icons for an input control device according to some embodiments. FIG. 8A illustrates a directional icon 200 that indicates movement of the input control device 36 is constrained in all degrees of freedom. For example, if the directional icon 200 is displayed with the selection of a menu option in the menu 110, the selected menu option may be actuated only if the surgeon S presses a switch on the input control device 36. The camera icon 112a, for example, may additionally be actuated if the surgeon S presses a switch 80 on the input control device 36. In alternative embodiments, the directional icon 200 indicates that movement of the input control device 36 is constrained in five degrees of freedom. In such embodiments, the camera icon 112a, for example, may be actuated by moving the input control device in the Z-direction (i.e., along the axis A1 in FIG. 2).

Figure 8B:
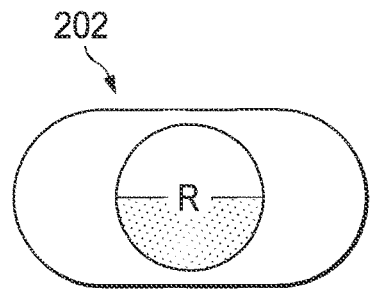
Figure 8C:
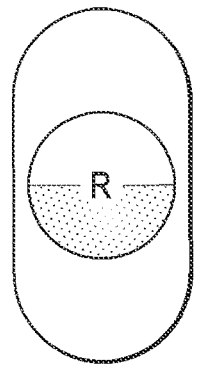
Figure 8D:
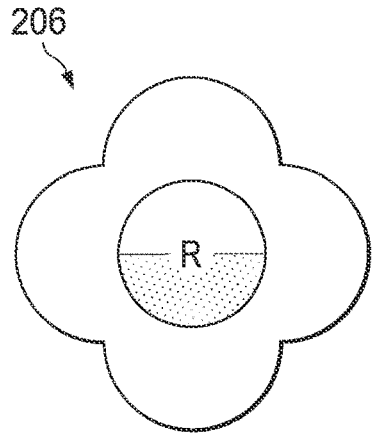
Figure 9A:
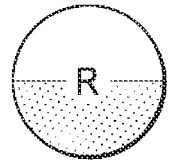
FIGS. 9A-9C are directional icons for an input control device according to some embodiments.
Figure 9B:
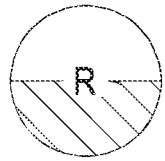
Figure 9C:
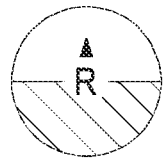

FIG. 8B illustrates a directional icon 202 that indicates the input control device 36 is constrained to move only in a translational direction (i.e., left and right along the axis A3 in FIG. 2) corresponding to the X-direction in the image 102 space. FIG. 8C illustrates a directional icon 204 that indicates the input control device 36 is constrained to move only in a translational direction (i.e., up and down along the axis A2 in FIG. 2) corresponding to the Y-direction in the image 102 space. The directional icon 204 is substantially similar to the directional icons 106a and 106b. FIG. 8l) illustrates a directional icon 206 that indicates the input control device 36 is constrained to move in only two translational directions (i.e., left/right along axis A3 and up/down along axis A2) corresponding to the X and Y-directions in the image 102 space. The directional icon 206 is substantially similar to the directional icons 114, 122, and 126.

FIG. 9A illustrates a directional icon 208 that indicates the input control device 36 is free from constraints in a plane corresponding to the X-Y plane in the image 102 space but is constrained from moving in any other direction. FIG. 99 illustrates a directional icon 210 that indicates the input control device 36 is free from constraints with respect to three-dimensional translational motion but is constrained to prevent rotational motion. FIG. 9C illustrates a directional icon 212 that indicates the input control device 36 is not constrained in any degree of freedom. Thus, the input control device 36 is free to move in three translational directions and is free to rotate about the three rotational axes.

Figure 10:
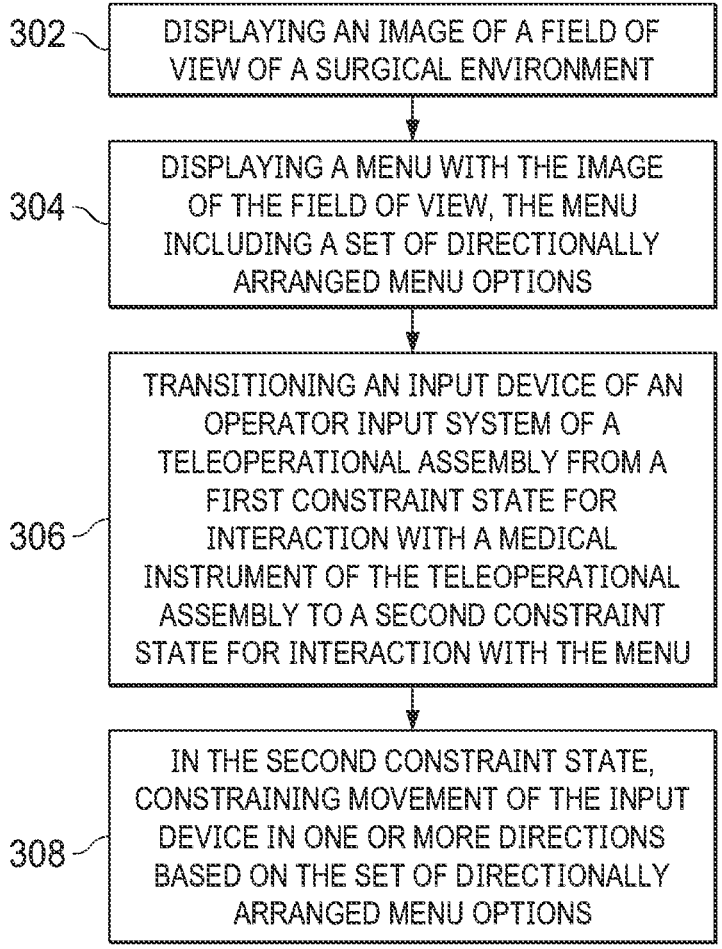
FIG. 10 is a flowchart of a method for transitioning into a graphical user interface mode to allow a user to interface with a graphical menu according to some embodiments.

Ha 10 is a flowchart illustrating a method 300 for constraining movement of the input control device 36 used to interface with the graphical menu 110. The method 300 is illustrated as a set of operations or processes 302 through 308 and is described with continuing reference to the preceding figures. Not all of the illustrated processes 302 through 308 may be performed in all embodiments of method 300. Additionally, one or more processes that are not expressly illustrated in FIG. 10 may be included before, after, in between, or as part of the processes 302 through 308. In some embodiments, one or more of the processes 302 through 308 may be implemented, at least in part, in the form of executable code stored on non-transitory, tangible, machine-readable media that when run by one or more processors (e.g., the processors of a control system) may cause the one or more processors to perform one or more of the processes. In one or more embodiments, the processes 302 through 308 may be performed by the control system 20.

At a process 302, an image (e.g., the image 102) of a field of view of a surgical environment (e.g., the surgical environment 100) is displayed. At a process 304, a menu (e.g., the graphical menu 110) is displayed with the image 102 of the field of view. The menu includes a set of directionally arranged menu options which may include displayed menu options such as primary menu options 112a-112e; secondary menu options 118, 119, 120; or secondary menu options in the form of brightness levels selectable with the slider bar 130. The menu may additionally or alternatively include a directionally arranged menu option which is not displayed, such as a camera activation menu option described in FIG. 5.

At a process 306, an input device (e.g., the input control device 36) of an operator input system (e.g., the operator input system 16) of a teleoperational assembly (e.g., the teleoperational assembly 12) is transitioned from a first constraint state for interaction with a first medical instrument (e.g., the instrument 30b) of the teleoperational assembly to a second constraint state for interaction with the menu 110. In several examples, the first constraint state may be referred to as a non-menu mode, a non-GUI mode, an instrument control mode, or a "following" operational mode in which the movement of the instrument 30b, for example, follows the movements of the user's hand in the input control device 36 associated with the instrument 30b. In several embodiments, the second constraint state may be referred to as a GUI mode, a menu mode, or a menu control mode in which movement of the user's hand in the associated input control device 36 is decoupled from movement of the instrument 30b and the manipulator arm 51. In further embodiments, the input control device 36 may be transitioned to a third constraint state where the input control device 36 may control the imaging device 28.

In several embodiments, the teleoperational assembly 12 is transitioned from the non-menu mode to the menu mode when an operator input device of the operator input system 16 is activated. The operator input device may be any one or more of the input control device(s) 36, the input control device(s) 37, a clutch device, a button, a switch (e.g., switch 60, 80), or any other input device. In some embodiments, the clutch device is a pedal (e.g., a clutch pedal), which may be any one of the input control devices 37 of the operator input system 16. In other embodiments, the clutch device may be any other input device, such as a button or a switch (e.g., switch 60, 80), for example. A clutch device may be any input that initiates or terminates a menu mode. Alternatively or additionally, a menu mode may be associated with a clutch mode of the teleoperational assembly that disconnects the surgeon input devices from the patient-side instruments. In further embodiments, the teleoperational assembly 12 may be transitioned from the non-menu mode to the menu mode when a gestural input is detected. For example, as the teleoperational system enters or exits the clutch mode, it may simultaneously enter or exit the menu mode, respectively. In some examples, the control system 20 may detect a gestural input of one or more of the input control devices 36. The teleoperational assembly 12 may be transitioned from the non-menu mode to the menu mode (or from the menu mode to the non-menu mode) when a gestural input is detected in combination with the activation of any one or more of the above operator input devices.

For exemplary purposes only, the following discussion will be made with reference to the clutch pedal. It is to be understood that this discussion similarly applies to any of the operator input devices discussed above. In some examples, the menu mode is entered when the surgeon S steps on the clutch pedal and keeps the clutch pedal depressed. While the clutch pedal remains depressed, control of the instrument 30b by the input control device 36 is suspended. The input control device 36 may move freely without causing corresponding movement of the instrument 30b. In the menu mode, movement of the grip actuators 78 of the input control device 36 is decoupled from the movement of the instrument 30b end effector. In some embodiments, the information fields 104a, 104b, 104c appear in the field of view of the surgical site upon entry into the menu mode. In other embodiments, the information fields 104a, 104b, 104c are also visible in the image 102 when the teleoperational assembly 12 is in the non-menu mode.

At a process 308, in the second constraint state, movement of the input device is constrained in one or more directions based on the set of directionally arranged menu options. As described in the above embodiments, when the teleoperational assembly 12 enters the menu mode, movement of the input control devices 36 is constrained based on the directional arrangement of the menu options which may include displayed menu options such as primary menu options 112a-112e; secondary menu options 118, 119, 120; or secondary menu options in the form of brightness levels selectable with the slider bar 130. Movement of the input control devices 36 may also be constrained based on the directional arrangement of menu options which are not displayed, such as a camera activation menu option described in FIG. 5. The movement of the input control devices 36 may be constrained by one or more haptic constraints. In several embodiments, the input control devices 36 may be free to translate in directions corresponding to the X-direction and/or the Y-direction in the image 102 space. The surgeon S may then interact with the menu 110 by moving cursor 113 in the X and Y-directions. By constraining movement to the X and Y-directions, the surgeon S can interact with the menu 110 without the need to adjust the position of his or her hands. This prevents the surgeon S from being required to move his or her hands into an uncomfortable position when navigating the menu 110. Additionally, this movement constraint allows for a quicker and easier transition from movement of the input control devices 36 in the non-menu mode to movement of the input control devices 36 in the menu mode. In some embodiments, the directional arrangement of the menu options allows the input control device 36 to be moved along additional axes within a plane corresponding to the X-Y plane in the image 102 space. For example, the menu options may be radially arranged such that the input control device 36 may be allowed to move along axes in the input control device 36 space that corresponds to axes in the image 102 space that are angled 45 degrees and 135 degrees from the X-axis. It is to be understood that the input control device 36 may be moved along any other axis corresponding to an axis in the X-Y plane of the image 102 space.

Optionally, when the surgeon S is finished interacting with the menu 110, the teleoperational assembly 12 is transitioned from the menu mode back to the non-menu mode. For example, the transition from the menu mode to the non-menu mode may occur when the clutch pedal of the operator input system 16 is deactivated. This may occur when the clutch pedal is released (i.e., the surgeon S removes his or her foot from the clutch pedal). When the clutch pedal is released, control of the instrument 30b by the input control device 36 is returned. Movement of the input control device 36 causes corresponding movement of the instrument 30b, and movement of the grip actuators 78 of the input control device 36 is coupled to the movement of the instrument 30b end effector.

In alternative embodiments, the teleoperational assembly 12 is transitioned from the non-menu mode to the menu mode when the surgeon S steps on and then releases the clutch pedal. After the clutch pedal is released, control of the instrument 30b by the input control device 36 is suspended. The input control device 36 may move freely without causing corresponding movement of the instrument 30b. In such alternative embodiments, when the surgeon S is finished interacting with the menu 110, the teleoperational assembly is transitioned from the menu mode back to the non-menu mode when the clutch pedal of the operator input system. 16 is depressed and then released. For example, the surgeon S steps on and then releases the clutch pedal. When the clutch pedal is depressed and released, control of the instrument 30b by the input control device 36 is returned.

In alternative examples, the clutch pedal may have a dual purpose. For example, the clutch pedal may be used as a master clutch pedal to allow movement of the input control devices 36 in the non-menu mode, and the clutch pedal may also be used to enter the menu mode. In such examples, the teleoperational assembly 12 is transitioned from the non-menu mode to the menu mode when the surgeon S steps on the clutch pedal, keeps the clutch pedal depressed, and then the input control devices 36 are not moved within a threshold amount of time after the clutch pedal is depressed. The lack of movement of the input control device 36 after the depression of the clutch pedal may indicate that the surgeon S wants to enter the menu mode. In some examples, the threshold amount of time after the clutch pedal is depressed within which the input control device 36 must not be moved to enter the menu mode is 200 milliseconds. However, the threshold amount of time may be set to any desired amount of time. After the input control device 36 has remained stationary within the threshold amount of time after the clutch pedal was depressed, control of the instrument 30b by the input control device 36 is suspended. The input control device 36 may move freely without causing corresponding movement of the instrument 30b.

In such alternative examples, when the surgeon S is finished interacting with the menu 110, the teleoperational assembly is transitioned from the menu mode back to the non-menu mode when the clutch pedal of the operator input system 16 is released. For example, the surgeon S takes his or her foot off the clutch pedal. When the clutch pedal is released, control of the instrument 30b by the input control device 36 is returned.

In further alternative embodiments, the teleoperational assembly 12 is transitioned from the non-menu mode to the menu mode when the surgeon S steps on the clutch pedal, releases the clutch pedal, and then the input control devices 36 are not moved within a threshold amount of time after the clutch pedal is released. The lack of movement of the input control device 36 after the release of the clutch pedal may indicate that the surgeon S wants to enter the menu mode. In some examples, the threshold amount of time after the clutch pedal is released within which the input control device 36 must not be moved to enter the menu mode is 200 milliseconds. However, the threshold amount of time may be set to any desired amount of time. After the input control device 36 has remained stationary within the threshold amount of time after the clutch pedal was released, control of the instrument 30b by the input control device 36 is suspended. The input control device 36 may move freely without causing corresponding movement of the instrument 30b.

In such alternative embodiments, when the surgeon S is finished interacting with the menu 110, the teleoperational assembly is transitioned from the menu mode back to the non-menu mode when the clutch pedal of the operator input system 16 is depressed and then released. For example, the surgeon S steps on and then releases the clutch pedal. When the clutch pedal is depressed and released, control of the instrument 30b by the input control device 36 is returned.

In this disclosure, specific words chosen to describe one or more embodiments and optional elements or features are not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes include various special device positions and orientations. The combination of a body's position and orientation define the body's pose.

In addition, the singular forms "a", "an", and "the" are intended to include the plural forms as well, unless the context indicates otherwise. And the terms "comprises," "comprising," "includes," "has," and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. The auxiliary verb "may" likewise implies that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

Various instruments and portions of instruments have been described in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Although some of the examples described herein refer to surgical procedures or instruments, or medical procedures and medical instruments, the techniques disclosed optionally apply to non-medical procedures and non-medical instruments. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

Further, although some of the examples presented in this disclosure discuss teleoperational robotic systems or remotely operable systems, the techniques disclosed are also applicable to computer-assisted systems that are directly and manually moved by operators, in part or in whole. A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller" or "control system," are analogous.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
a teleoperational manipulator configured to control operation of a medical instrument in a surgical environment;
an operator input system including a plurality of input devices; and
a processing unit including one or more processors, wherein the processing unit is configured to:
display an image of a field of view of the surgical environment;
display a menu including a set of directionally arranged menu options and an icon; and
transition an input device of the plurality of input devices from a first constraint state for interaction with the medical instrument to a second constraint state for interaction with the menu, wherein in the second constraint state, the input device is constrained to move in one or more directions based on the set of directionally arranged menu options, and wherein the icon indicates which of the plurality of input devices is the constrained input device.

2. The system of claim 1, further comprising a display device for displaying the image of the field of view and the menu.

3. The system of claim 1, wherein in the second constraint state, the one or more directions in which the input device is constrained to move are determined independent of an orientation of the input device.

4. The system of claim 1, further comprising a teleoperational assembly, wherein the teleoperational assembly comprises an operator input device, and wherein the processing unit is further configured to transition the input device from the first constraint state to the second constraint state in response to a determination that the operator input device is activated.

5. The system of claim 4, wherein activation of the operator input device includes receiving, by the processing unit, an indication that the operator input device is depressed.

6. The system of claim 4, wherein activation of the operator input device includes receiving, by the processing unit, a first indication that the operator input device is depressed and released.

7. The system of claim 4, wherein activation of the operator input device includes:
receiving, by the processing unit, an indication that the operator input device is depressed; and
receiving, by the processing unit, an indication that the input device is not moved within a predetermined time interval after the operator input device is depressed.

8. The system of claim 4, wherein the operator input device includes at least one of a pedal, a switch on the input device, or a clutch device.

9. The system of claim 1, wherein in the first constraint state, the input device is movable in six degrees of freedom.

10. The system of claim 1, wherein in the second constraint state, the input device is movable in three degrees of freedom.

11. The system of claim 1, wherein in the second constraint state, the input device is movable in two degrees of freedom.

12. The system of claim 1, wherein in the second constraint state, the input device is movable in one degree of freedom.

13. The system of claim 1, wherein in the second constraint state, a haptic constraint limits movement of the input device in the one or more directions.

14. The system of claim 13, wherein after the input device is moved away from a starting position, the haptic constraint guides the input device back to the starting position along a linear path.

15. The system of claim 13, wherein after the input device is moved away from a starting position along a movement path, the haptic constraint guides the input device back to the starting position along the movement path.

16. The system of claim 1, wherein a haptic feedback provides an indication of a movement of the input device away from a starting position.

17. The system of claim 16, wherein the movement includes movement from one menu option from the set of directionally arranged menu options to another menu option from the set of directionally arranged menu options.

18. The system of claim 16, wherein the movement includes movement away from a menu option from the set of directionally arranged menu options to actuate the menu option.

19. The system of claim 1, wherein the icon further indicates the one or more directions in which the input device is constrained to move.

20. The system of claim 1, wherein the processing unit if further configured to display a movable indicator at a control location within the set of directionally arranged menu options, wherein the input device is constrained to move in the one or more directions based on the control location within the set of directionally arranged menu options.

* * * * *

UNITED STATES PATENT AND TRADEMARK OFFICE
CERTIFICATE OF CORRECTION

| | | |
|---|---|---|
| PATENT NO. | : 12,121,309 B2 | Page 1 of 1 |
| APPLICATION NO. | : 17/799766 | |
| DATED | : October 22, 2024 | |
| INVENTOR(S) | : Tabish Mustufa et al. | |

It is certified that error appears in the above-identified patent and that said Letters Patent is hereby corrected as shown below:

In the Specification

Column 9, Line 28, change "1.04c" to -- 104c --

Column 9, Line 43, change "104h" to -- 104b --

Column 11, Line 34, change "301" to -- 30b --

Column 12, Line 23, change "104bl" to -- 104b --

Column 12, Line 41, change "301" to -- 30b --

Column 12, Line 42, change "301" to -- 30b --

Column 15, Line 34, change "69" to -- 6B --

Column 16, Line 50, change "104" to -- 104b --

Column 17, Line 26, "36 up the" should read -- 36 up (e.g., the --

Column 17, Line 39, change "threes" to -- forces --

Column 18, Line 10, change "81" to -- 8D --

Column 18, Line 20, change "99" to -- 9B --

Column 18, Line 29, change "Ha" to -- FIG. --

Signed and Sealed this
Tenth Day of December, 2024

Katherine Kelly Vidal
*Director of the United States Patent and Trademark Office*